United States Patent [19]

Talwar

[11] 4,191,746

[45] Mar. 4, 1980

[54] STERILIZATION PROCESS FOR MAMMALS

[75] Inventor: Gursaran P. Talwar, New Delhi, India

[73] Assignee: All India Institute of Medical Sciences, New Delhi, India

[21] Appl. No.: 18,624

[22] Filed: Mar. 8, 1979

[51] Int. Cl.² .............................................. A61K 39/04
[52] U.S. Cl. ...................................................... 424/92
[58] Field of Search ........................................... 424/92

[56] References Cited

PUBLICATIONS

Dixit, V.P. et al. J. Anat. Soc. India Vol. 25 (3), pp. 115-117 (1976), Chemical Sterilization of male dog: A Single Intratesticular injection of Alpha-Chlorohydrin. Dixit, V.P. Acta Evr. Fortil. vol. 7 (2), pp. 175-179 (1976), A Reversible Chemical Sterilization of Male Langurs: A Single Intratesticular Injection of alpha-Chlorohydrin.

*Primary Examiner*—Shep K. Rose
*Attorney, Agent, or Firm*—Sim & McBurney

[57] ABSTRACT

Aspermatogenesis is achieved in mammalian species without disturbance of libido and hormone level by intratesticular injection of Bacillus of Calmette and Guerin. The procedure is applicable to a wide variety of mammalian species.

6 Claims, No Drawings

STERILIZATION PROCESS FOR MAMMALS

FIELD OF INVENTION

The present invention is directed to sterilization of mammalian species.

BACKGROUND TO THE INVENTION

Sterilization of male animals, practised to limit reproduction in stray animals and livestock, is usually effected by castration. Sterilization operations involving vasectomy and vasligation are also effected on male humans.

The extreme nature of these procedures and the necessity for skilled surgical operation has led to suggestions of alternative approaches to mammalian sterilization. For example, a number of hormonal formulations, consisting of anti-androgens and androgens, have been suggested for suppression of spermatogenesis or interfering with the maturation of sperm.

In early clinical trials, these formulations, however, have exhibited adverse side effects, including, loss of libido and a dependence on a continual intake of hormonal steroids.

SUMMARY OF INVENTION

The present invention enables aspermatogenesis to be achieved in mammalian species without disturbance of libido and hormone levels. The invention avoids the necessity for surgical operation, provides a humane approach to the sterilization of males and the procedure may be effected by semi-skilled personnel.

In accordance with the present invention, Bacillus of Calmette and Guerin (BCG) is intratesticularly injected in an amount at least effective to achieve aspermatogenesis.

GENERAL DESCRIPTION OF INVENTION

BCG is widely known and is used as a vaccine in human and other animals for protection against tuberculosis. It has never been suggested, heretofore, as far as I am aware, that it is possible to achieve aspermatogenesis by intratesticular injection of BCG into male animals. The novel utility of BCG for aspermatogenesis is entirely unexpected, having regard to the known utility and properties of BCG.

While I do not wish to be bound by any theory as to the manner in which the BCG produces aspermatogenesis in this invention, there are indications in the tests I have conducted that the BCG creates, within the testicle, an inflammatory response which brings to local sites the cells competent for eliciting immune response. The immune response is generated selectively against the antigens present on spermacytes and the intermediate developing stages of spermatozoa, so that spermatogenesis is blocked.

The method has been found to be effective against all species tested, including such widely-different species as rats, guinea pigs, rabbits, dogs, rams, bucks and rhesus monkeys. Preliminary testing also demonstrates the effectiveness and utility of the procedure in blocking spermatogenesis in humans.

No adverse side effects to the treatment were observed. In all the test cases, the animals retained their libido, and blood androgen levels were unchanged by the procedure. Histological observations also showed the normalcy of Sertoli and Leydig cells, the latter being confirmed by a rise in plasma androgen levels after administration of gonadotropins.

In addition, no apparent toxicity was observed, no decline in animal body weight or other sign of morbidity were observed, and blood chemistry remained normal, indicating the normalcy of endocrine, organ and metabolic functions.

The present invention has considerable practical significance both with respect to control of reproduction of stray animals and livestock and with respect to human population control. The bacillus is widely available and relatively inexpensive, so that large scale implementation may be practical.

The apparent absence of any adverse side effects, especially the problematical side effects of loss of libido and androgens inherent in prior procedures, renders the procedure especially advantageous.

The dosage used in the intra-testicular injection is at least the quantity effective to achieve aspermatogenesis, and usually is well in excess of that minimum level. The minimum quantity used varies depending on the species requiring sterilization. The quantity of BCG used generally is at least about 3 times the normal human dose for anti-tuberculosis injections, or at least about $1.5 \times 10^7$ organisms. Quantities in excess of 1000 times the human dose ($5 \times 10^{10}$ organisms) generally do not produce any added benefit, although may be used, if desired. The injection is effective in a short period of time, generally less than 30 days.

EXAMPLES

EXAMPLES I—Dogs

Samples of BCG vaccine, consisting of quantities of lyophilized live bacilli from 7 to 110 times the human dose (0.35 to 5.5 mg, $3.5 \times 10^8$ to $55 \times 10^8$ organisms) suspending in increasing quantities of saline solution (0.15 wt% NaCl in water) from 0.05 ml to 0.3 ml, were injected into each testicle of a number of adult male dogs weighing between 13 kg and 20 kg. Doses greater than 14.0 mg/testicle were found to have no additional or faster effect. Sterilization, as determined by ejaculation of sperm-free semen, occurred in 21 to 30 days post injection.

There were no side-effects as evidenced by determination of the following parameters:

(a) Body weight constant for up to 10 months.

(b) Libido intact for at least 10 months.

(c) Semen volume essentially unchanged.

(d) Plasma testerone and cortisol essentially normal.

(e) Haemotology, including haemoglobin, haemotocrit and leucocyte count unaltered.

(f) Liver functions, including bilirubin, ALP, SGPT and LDH, were unaltered.

(g) Kidney functions such as blood urea and serum creatinine were unchanged.

(h) Other metabolic functions that were monitored and found to be unchanged were, blood glucose, serum cholesterol, total serum proteins, serum albumin and serum globulins.

EXAMPLE II—Rams

Three rams were given $1,000 \times$ normal human dose of BCG (about $50 \times 10^9$ organisms) in each testicle. Semen samples showed that after a maximum of four weeks there were no viable sperm remaining. Three control rams who were kept in the same area and uninjected showed no change in sperm count or motility.

EXAMPLE III—Non-human primates.

Two male monkeys were injected with BCG vaccine (50 to 100×normal human dose, 2.5 to 5 mg, $2.5 \times 10^9$ to $5 \times 10^9$ organisms) in each testicle. Monitoring of metabolic functions showed that the monkeys remained perfectly healthy. Histological examination on biopsy showed that spermatogenesis has ceased.

EXAMPLE IV—Other species

A number of other species were treated with BCG vaccine in doses varying from 3 to 1,000 times the normal human dose. These included rats, guinea pigs and rabbits. In all cases metabolic functions were unchanged and histological examination of biopsy specimens showed that spermatogenesis had ceased. The average dose was 10 times the normal human dose.

SUMMARY OF DISCLOSURE

In summary of this disclosure, the present invention is directed to a sterilization procedure which involves an entirely unexpected use of BCG. Modifications are possible within the scope of the invention.

What I claim is:

1. A method of sterilizing mammalian species, which comprises intra-testicularly injecting Bacillus of Calmette and Guerin into each testicle of sperm-producing males of the species in an amount at least effective to achieve aspermatogenesis.

2. The method of claim 1 wherein said Bacillus is used in an amount of at least about $1.5 \times 10^7$ organisms per testicle.

3. The method of claim 1 wherein said Bacillus is used in an amount of at least about 3 times the normal human dose for anti-tuberculosis injections.

4. The method of claim 2 wherein said Bacillus is used in an amount up to about $50 \times 10^9$ organisms per testicle.

5. The method of claim 1, 2, 3, or 4 wherein said mammalian species are selected from dogs, rams, non-human primates, rats, guinea pigs and rabbits.

6. The method of claim 1, 2, 3, or 4 wherein said mammalian species is dogs.